Figures 1, 2:
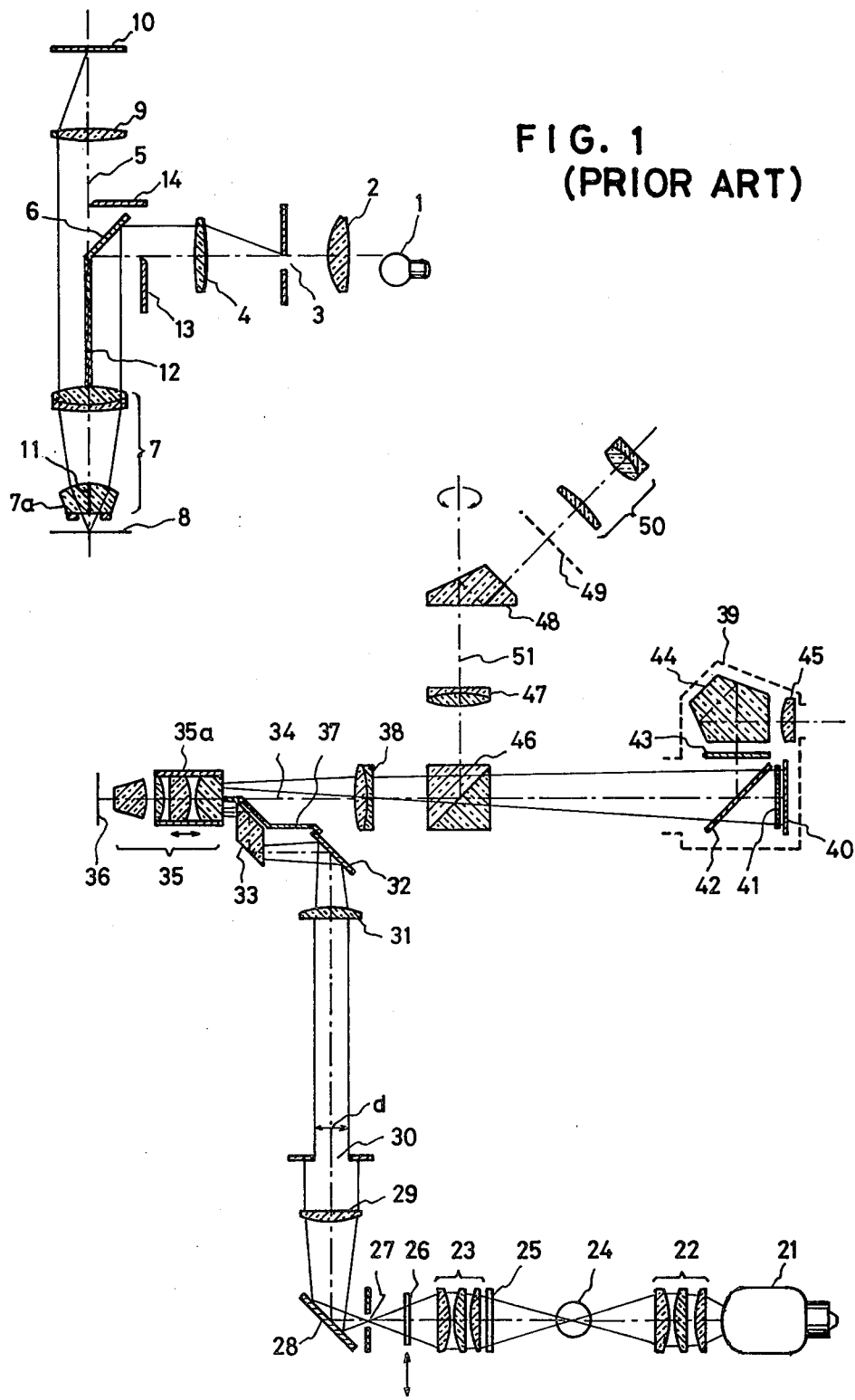

United States Patent [19]

Abe

[11] Patent Number: 4,479,700
[45] Date of Patent: Oct. 30, 1984

[54] MICROSCOPE

[76] Inventor: Kuniomi Abe, 870-72, Aza-Shingahira, Higashitarumi-cho, Tarumi-ku, Kobe, Japan

[21] Appl. No.: 387,164

[22] Filed: Jun. 10, 1982

[30] Foreign Application Priority Data

Jun. 22, 1981 [JP] Japan .................................. 56-97320

[51] Int. Cl.³ ............................................ G02B 21/06
[52] U.S. Cl. ................................................. 350/523
[58] Field of Search .................. 350/523, 527; 351/205

[56] References Cited

U.S. PATENT DOCUMENTS 4,386,830 6/1983 Stankewitz et al. ................. 350/527

FOREIGN PATENT DOCUMENTS 2034499 4/1980 United Kingdom .

Primary Examiner—John K. Corbin
Assistant Examiner—Lynn Vandenburgh Kent
Attorney, Agent, or Firm—Eugene E. Geoffrey, Jr.

[57] ABSTRACT

A microscope, such as an eyebell microscope used for observing an eyeball cornea, eye-ground and the like, which is arranged to illuminate an object for observation with a light beam projected through one half of the objective lens and to form an image of the object with the light reflected back through the other half of the same objective lens, wherein a special iris for confining the illuminating light beam is inserted in the illuminating optics in order to prevent the illuminating light from mixing in the image forming light and reducing contrast of the image.

2 Claims, 2 Drawing Figures

MICROSCOPE

This invention relates to a microscope, such as an eyeball microscope, arranged to illuminate the object for observation with a light beam projected through one half of the objective lens and to form a magnified image with the light reflected back from the object through the other half of the same objective lens.

An example of this type of microscope is described in the opened British patent specification No. 2,034,499. In this microscope, an illuminating light emitted from a light source is collimated into a parallel light beam and led into the bodytube by a reflecting mirror disposed on one side of the optical axis, whereby the illuminating light beam passes through one half of the objective lens towards the object for observation and the light reflected from the object, which will be hereinunder called "imaging light", passes in the opposite direction through the other half of the same objective lens and forms an image on a photographic filmm, for example. Between the halves of the objective lens, there is disposed a light shielding layer for preventing the illuminating light from mixing in the imaging light. In such prior art microscope, however, the illuminating light can be reflected and/or scattered within the bodytube and then mixed in the imaging light to reduce contrast of the image, since the whole region on one side of the optical axis is used as a path for the illuminating light.

Accordingly, an object of this invention is to modify the structure of the above mentioned prior art microscope to remove the above mentioned disadvantage.

This object is attained by disposing a special iris for confining the illuminating light beam to a part of the above mentioned half of the objective lens in the vicinity of a point which is conjugate with the entrance pupil of the objective lens in accordance with the principle of this invention.

The object and features of this invention will be well understood by reading the following description with reference to the accompanying drawings.

IN THE DRAWINGS

FIG. 1 is a schematic diagram representing an optical system of a prior art microscope; and FIG. 2 is a schematic diagram representing an optical system of an embodiment of the microscope according to this invention.

Referring to FIG. 1 which corresponds to FIG. 2 of the above mentioned British patent specification, the light emitted from a light source 1 is collected by a condenser lens 2 to pass through a slit 3 and then collimated by a collimater lens 4 into a parallel light beam. The beam is reflected by a mirror 6 disposed on one side of the optical axis 5 of the microscope and led into this half side of the bodytube to illuminate an object plane 8 through one half of an objective lens 7. The imaging light reflected back from the object plane 8 passes through the other half of the objective lens 7 and travels along the other half of the bodytube to form an image with the aid of an imaging lens 9 on a photographic film 10. A tip member 7a of the objective lens 7 is divided in two parts and a light shielding layer 11 is disposed in the split plane of the tip member 7a so as to prevent the illuminating light reflected by the tip surface of the tip member 7a from mixing in the imaging light. A light shielding wall 12 disposed along the optical axis of the microscope and knife edges 13 and 14 disposed respectively in the paths for illuminating and imaging lights serve to prevent the illuminating and imaging lights from entering the other halves mutually across the optical axis 5. However, since, as seen from the drawing, the whole region on one side of the optical axis 5 of the microscope is utilized as the illuminating light path, the illuminating light reflected or scattered in the bodytube can stray off into the imaging light to reduce contrast of the image, especially when the slit width is increased.

Referring next to FIG. 2 representing a preferred embodiment of this invention, the light emitted from a light source 21 is collected by a condenser lens 22 and then collected again by another condenser lens 23. A strobotron 24 is disposed at the point of collection of the condenser lens 22 and a thermal protection filter 25 is disposed in this side of the condenser lens 23. A monochromatic filter 26 is disposed detachably on that side of the condenser lens 23 and a semi-circular or arcuate iris 27 is disposed at the point of collection of the condenser lens 23.

After passing through the iris 27, the illuminating light is reflected by a mirror 28 and then passes through a lens 29 and a variable width slit 30. The variable width slit 30 is elongated in the direction normal to the paper plane and has an adjustable width d. This slit 30 is positioned in the vicinity of the conjugate focus of the object plane 36 provided by undermentioned slit projecting lens 31 and objective lens 35.

After passing through the slit 30, the illuminating light passes through the slit projecting lens 31 and is reflected by a mirror 32 and a rhombic prism 33 to enter the main bodytube of the microscope. Then, the illuminating light travels substantially in parallel to the optical axis 34 of the microscope and passes through the objective lens 35 to illuminate the object plane 36 elongatedly in the direction normal to the paper plane. On the other hand, the image of the iris 27 is formed by the lens 29 and the slit projecting lens 31 in the vicinity of the entrance pupil of the objective lens 35 so as not to contact the optical axis 34 and the bodytube. A light shield 37 is also used as a support frame of the mirror 32 and the prism 33.

The objective lens 35 has a floating structure and can keep in constant contact with a cornea regardless of forward and backward movement of the face of an observed person. Only its back lens group 35a can be moved along the optical axis for focus adjustment.

The imaging light having passed through the objective lens 35 forms an image on a photographic film 40 within a camera 39 with the aid of an imaging lens 38. In this embodiment, the camera 39 is of a conventional single-lens reflex type, which includes a shutter 41 and a movable mirror 42 in front of the film 40, and the image is formed on a screen 43 when the movable mirror 42 is in the position as shown. The image on the screen 43 can be observed through a pentagonal prism 44 and a finder lens 45.

The imaging light is branched by a half-mirror 46 between the imaging lens 38 and the camera 39 and passes through a contraction lens 47 and a declination prism 48 to form an image on a plane 49. This image can be observed through an eyepiece 50. The contraction lens 47 serves to change the magnification factor of the image formed on the plane 49 so as to be suitable for observation. The declination prism 48 is arranged to be rotatable about the branched optical axis 51 together with the eyepiece 50.

The above mentioned arrangement of microscope, wherein one side of the optical axis 34 is used as the path for illuminating light and the other side thereof is used as the path for imaging light, is similar to that of the prior art microscope as shown in FIG. 1. However, in the microscope of this invention, the illuminating light enters the objective lens 35 with sufficient convergence since the image of the iris 27 is formed in the vicinity of the entrance pupil of the objective lens 35, while the illuminating light of the prior art enters the objective lens 7 throughout the whole area of one half thereof.

Within the interior of the optical equipment, scattering and reflection of light occur unavoidably at the lens surfaces, bodytube inner surface and the like and the amount of scattering and reflection increases in proportion with the amount of incidence. In the microscope of FIG. 1, the light beam illuminating the photographable area of the object plane is only a part of the illuminating light entering the objective lens 7 and the illuminating light directed to the outside of this area serves no function other than increasing the amount of scattering and reflection to reduce contrast of the resultant photograph.

According to this invention, however, the illuminating light entering the objective lens 35 is confined by the iris 27 so as to pass through only a part of the lower half of the objective lens 35 in FIG. 2 and, therefore, scarcely impacts the split plane of the objective lens 35 and the bodytube inner surface. Accordingly, it is possible to reduce the amount of scattering and reflection within the optical system to improve contrast of the observed and photographed image.

Moreover, the contrast can be improved further if the width d of the slit 30 is made variable and adjusted as occasion demands. With this improved contrast over the prior art, this invention can exhibit an especially significant effect when embodied in the eyeball microscope for observing cornea cells and the like.

I claim:

1. A microscope, arranged to illuminate an object for observation with a source of illuminating light producing a light beam which passes through one half of an objective lens divided in two halves by a split plane substantially including the optical axis of said microscope and to effect magnified observation or photography of said object with an imaging light passing through the other half of said objective lens in a direction opposite to said illuminating light with negligible light scattering which interferes with the image; characterized by an iris fixedly positioned in the vicinity of a point which is conjugate with the entrance pupil of said objective lens and having a configuration conforming substantially with the configuration of said one half of said objective lens for confining incidence of said illuminating light into said objective lens to a part of said one half, a lens system for focusing the light source at the position of the iris, said lens system including a first condenser lens adjoining said light source, a strobotron positioned at the point of collection of light from said first condenser lens, a thermal protection filter following said strobotron, and a second condenser lens following said thermal protection filter, optical means in close proximity to said objective lens for directing said illuminating light through said lens and means in close proximity to said optical means and said objective lens for shielding said illuminating light from said imaging light.

2. A microscope, according to claim 1, characterized by a beam limiting variable-width slit disposed between said iris and said objective lens and adjustable to achieve maximum contrast.

* * * * *